United States Patent
Strauss et al.

(10) Patent No.: US 11,440,963 B2
(45) Date of Patent: Sep. 13, 2022

(54) COMBINATION PDL1 AND TGF-BETA BLOCKADE IN PATIENTS WITH HPV+ MALIGNANCIES

(71) Applicant: The United States of America, as represented by the Secretary, Department of Health and Human Services, Bethesda, MD (US)

(72) Inventors: Julius Y. Strauss, Silver Spring, MD (US); James L. Gulley, Takoma Park, MD (US); Christian S. Hinrichs, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 92 days.

(21) Appl. No.: 16/612,495

(22) PCT Filed: May 8, 2018

(86) PCT No.: PCT/US2018/031501
§ 371 (c)(1),
(2) Date: Nov. 11, 2019

(87) PCT Pub. No.: WO2018/208720
PCT Pub. Date: Nov. 15, 2018

(65) Prior Publication Data
US 2020/0062849 A1 Feb. 27, 2020

Related U.S. Application Data

(60) Provisional application No. 62/503,405, filed on May 9, 2017.

(51) Int. Cl.
| | | |
|---|---|---|
| *C07K 16/28* | (2006.01) | |
| *A61K 39/395* | (2006.01) | |
| *A61P 35/00* | (2006.01) | |
| *A61K 45/06* | (2006.01) | |
| *C07K 14/71* | (2006.01) | |
| *C12N 15/62* | (2006.01) | |
| *C12N 15/86* | (2006.01) | |
| *A61K 39/00* | (2006.01) | |

(52) U.S. Cl.
CPC ...... *C07K 16/2827* (2013.01); *A61K 39/3955* (2013.01); *A61K 45/06* (2013.01); *A61P 35/00* (2018.01); *C07K 14/71* (2013.01); *C12N 15/62* (2013.01); *C12N 15/86* (2013.01); *A61K 2039/505* (2013.01); *C07K 2317/76* (2013.01); *C07K 2319/30* (2013.01); *C07K 2319/32* (2013.01)

(58) Field of Classification Search
None
See application file for complete search history.

(56) References Cited

FOREIGN PATENT DOCUMENTS

| WO | WO 2015/118175 A2 | 8/2015 |
|---|---|---|
| WO | WO 2016/057933 A1 | 4/2016 |

OTHER PUBLICATIONS

Lyford-Pike et al, Cancer Res; 2013, vol. 73, No. 6, pp. 1733-1741.*
Liu et al, (Clin Cancer Res;24(23); 6001-6014; 2018).*
Zhu et al, (Tumor Biol. (2016) 37:7075-7083).*
Mirzaei et al, (Reviews in Medical Virology, 2018; vol. 28; No. 2, e1967 pp. 1-14; https://doi.org/10.1002/rmv.1967).*
Lee et al., (The Journal of Biological Chemistry; 2002; vol. 277, No. 41; pp. 38557-3856).*
Tsai et al, (Journal for ImmunoTherapy of Cancer 10: e004601,2022; doi:10.1136/jitc-2022-004601).*
Chung et al., "Efficacy and Safety of Pembrolizumab in Previously Treated Advanced Cervical Cancer: Results From the Phase II KEYNOTE-158 Study," *Journal of Clinical Oncology*, 37(17): 1470-1478 (2019).
European Patent Office, International Search Report in International Patent Application No. PCT/US2018/031501 (dated Jul. 9, 2018).
European Patent Office, Written Opinion in International Patent Application No. PCT/US2018/031501 (dated Jul. 9, 2018).
Ferris et al., "Nivolumab for Recurrent Squamous-Cell Carcinoma of the Head and Neck," *N. Engl. J. Med.*, 375(19): 1856-1867 (2016).
Frenel et al., "Pembrolizumab in patients with advanced cervical squamous cell cancer: Preliminary results from the phase Ib KEYNOTE-028 study," *J Clin Oncol.*, 34(suppl; abstr 5515) (2016).
Frenel et al., "Safety and Efficacy of Pembrolizumab in Advanced, Programmed Death Ligand 1-Positive Cervical Cancer: Results From the Phase Ib KEYNOTE-028 Trial," *J. Clin. Oncol.*, 35(36): 4035-4041 (2017).
Hakenberg et al., "Chemotherapy in penile cancer," *Ther. Adv. Urol.*, 4(3): 133-138 (2012).
Kamran et al., "Primary tumor sidedness is an independent prognostic marker for survival in metastatic colorectal cancer: Results from a large retrospective cohort with mutational analysis," *Cancer Medicine*, 7: 2934-2942 (2018).
Levovitz et al., "TGFβ Receptor 1: An Immune Susceptibility Gene in HPV-Associated Cancer," *Cancer Res.* 74(23): 6833-6844 (2014).
Liu et al., "Increased expression of PD-L1 by the human papillomavirus 16 E7 oncoprotein inhibits anticancer immunity," *Molecular Medicine Reports*, 15(3): 1063-1070 (Mar. 1, 2017).
Mehra et al., "Efficacy and safety of pembrolizumab in recurrent/metastatic head and neck squamous cell carcinoma (R/M HNSCC): Pooled analyses after long-term follow-up in KEYNOTE-012," *J. Clin. Oncol.* 34(suppl; abstr 6012) (2016).

(Continued)

*Primary Examiner* — Bridget E Bunner
*Assistant Examiner* — Fozia M Hamud
(74) *Attorney, Agent, or Firm* — Leydig Voit and Mayer, Ltd.

(57) ABSTRACT

The invention provides a method of inhibiting a malignancy associated with human papilloma virus (HPV) comprising administering to a subject an agent that blocks PD-L1 and TGF-beta pathways, thereby inhibiting a malignancy associated with HPV in the subject.

22 Claims, No Drawings

(56) References Cited

OTHER PUBLICATIONS

Mehra et al., "Efficacy and safety of pembrolizumab in recurrent/metastatic head and neck squamous cell carcinoma: pooled analyses after long-term follow-up in KEYNOTE-012," *British Journal of Cancer*, 119: 153-159 (2018).

Nascimento De Oliveira et al., "Topotecan Use for Second-Line Treatment in Patients with Recurrent or Metastatic Cervical Cancer at Brazilian National Cancer Institute (INCA)," *Journal of Cancer Therapy*, 4: 1095-1099 (2013).

Ott et al., "Safety and antitumor activity of the anti-PD-1 antibody pembrolizumab in patients with recurrent carcinoma of the anal canal," *Ann. Oncol.*, 28(5): 1036-1041 (2017).

Patnaik et al., "Phase I study of MK-3475 (anti-PD-1 monoclonal antibody) in patients with advanced solid tumors," *2012 American Society of Clinical Oncology (ASCO) Annual Meeting*, Abstract # 2512), 2012.

Powell et al. "KEYNOTE-055: A phase II trial of single agent pembrolizumab in patients (pts) with recurrent or metastatic head and neck squamous cell carcinoma (HNSCC) who have failed platinum and cetuximab," *J. Clin. Oncol.*, 33(suppl; abstr TPS3094) (2015).

Reade et al., "Systemic therapy in squamous cell carcinoma of the vulva: current status and future directions," *Gynecologic Oncology*, 132: 780-789 (2014).

Song et al., "Dendritic cells with an increased PD-L1 by TGF-β induce T cell anergy for the cytotoxicity of hepatocellular carcinoma cells," *International Immunopharmacology*, 20(1): 117-123 (Mar. 4, 2014).

Strauss et al., "Phase 1 trial of M7824 (MSB0011359C), a bifunctional fusion protein targeting PD-L1 and TGF-β, in advanced solid tumors," *Clinical Cancer Research*, 24(6): 1287-1295 (Jan. 3, 2018).

Sunshine et al., "PD-1/PD-L1 inhibitors," *Curr. Opin. Pharmacol.*, 23: 32-38 (2015).

Tang et al., "EGFR tyrosine kinase inhibitors: difference in efficacy and resistance," *Current Oncology Reports*, 15(2): 98-104 (2013).

Terabe et al., "Blockade of only TGF-β 1 and 2 is sufficient to enhance the efficacy of vaccine and PD-1 checkpoint blockade immunotherapy," *OncoImmunology*, 6(5): e1308616 (May 4, 2017).

U.S. National Library of Medicine, "A Phase 1 Study of Nivolumab (BMS-936558) in Subjects With Advanced or Recurrent Malignancies (MDX1106-03)," ClinicalTrials.gov Identifier NCT00730639 (Aug. 2, 2008).

Venook et al., "Primary (1° C.) tumor location as an independent prognostic marker from molecular features for overall survival (OS) in patients (pts) with metastatic colorectal cancer (mCRC): Analysis of CALGB / SWOG 80405 (Alliance)," *J. Clin. Oncol.* 34, (suppl; abstr 3503) (2016).

Weber, *Semin. Oncol.*, "Immune checkpoint proteins: a new therapeutic paradigm for cancer—preclinical background: CTLA-4 and PD-1 blockade," 37(5): 430-4309 (2010).

Zhang et al., "Mammary-tumor-educated B cells acquire LAP/TGF-β and PD-L1 expression and suppress anti-tumor immune responses," *International Immunology*, 28(9): 423-433 (Feb. 19, 2016).

* cited by examiner

COMBINATION PDL1 AND TGF-BETA BLOCKADE IN PATIENTS WITH HPV+ MALIGNANCIES

CROSS-REFERENCE TO RELATED APPLICATIONS

This patent application is the U.S. National Phase of International Patent Application No. PCT/US2018/031501, filed May 8, 2018, which claims the benefit of U.S. Provisional Patent Application No. 62/503,405, filed May 9, 2017, each of which is incorporated by reference in its entirety herein.

STATEMENT REGARDING FEDERALLY SPONSORED RESEARCH OR DEVELOPMENT

This invention was made with Government support under project number Z01BC010666-12 by the National Institutes of Health, National Cancer Institute. The Government has certain rights in the invention.

BACKGROUND OF THE INVENTION

Metastatic or refractory/recurrent HPV associated malignancies (cervical, anal, oropharyngeal, vulvar, vaginal, penile, and squamous cell rectal cancer) are incurable and poorly palliated by standard therapies. For many of these diseases there is no standard second line therapy for advanced disease or second line chemotherapy for these disease yields a response rate less than 10-15% of the time (Nascimento de Oliveira et al., Journal of Cancer Therapy, 4: 1095-1099 (2013); Reade et al., Gynecologic Oncology, 132: 780-789 (2014); and Hakenberg et al., The Adv. Urol., 4(3): 133-138 (2012)).

Early evidence from single agent PD-1 inhibition in these diseases has shown a response rate in the range of 12-21%. Pembrolizumab was FDA approved for recurrent or metastatic head and neck squamous cell carcinoma (HNSCC) based upon a 17.7% response rate with response rates being similar in HPV positive and negative disease (Mehra et al., J. Clin. Oncol. 34(suppl; abstr 6012) (2016)). In particular, pembrolizumab has an overall response rate in metastatic cervical cancer and metastatic anal carcinoma of 17% (Frenel et al., J. Clin. Oncol., 35(36): 4035(2017), and Ott et al., Ann. Oncol., 28(5): 1036 (2017)). Pembrolizumab alone produces a 12.5% response rate in recurrent/metastatic cervical cancer (Frenel et al., J Clin Oncol., 34(suppl; abstr 5515) (2016)), 20% response rate in recurrent/metastatic squamous cell anal cancer (Frenel et al., J Clin Oncol., 34(suppl; abstr 5515) (2016)), and a 19.6% overall response rate in recurrent/metastatic head and neck squamous cell carcinoma (HNSCC) (Powell et al. J. Clin. Oncol., 33(suppl; abstr TPS3094) (2015)). Nivolumab alone produces a 21% response rate in refractory metastatic squamous cell anal cancer (Morris et al., J. Clin. Oncol. 34, (suppl; abstr 3503) (2016), and a 13.3% response rate in HNSCC patients (Ferris et al., N. Engl. J. Med., 375(19): 1856 (2016)).

In addition to the PD-1/PD-L1 pathway, some data suggests that the TGF-beta pathway may also play a role in HPV+ malignancies (Levovitz et al., Cancer Res. 74(23): 6833-44 (2014)). However, no agent targeting the TGF-beta pathway has been developed or employed to treat HPV-associated cancers.

Therefore, there is a desire for the identification of a new agent for treating HPV+ malignancies.

BRIEF SUMMARY OF THE INVENTION

The invention provides a method of inhibiting a malignancy associated with human papilloma virus (HPV) comprising administering an agent that blocks PD-L1 and TGF-beta pathways to a subject, thereby inhibiting a malignancy associated with HPV in the subject.

DETAILED DESCRIPTION OF THE INVENTION

The invention is predicated at least in part on the inventors' discovery that the blockade of the PD-L1 and TGF-beta pathways results in significantly higher response rates in patients with human papillomavirus (HPV)+ malignancies relative to current treatments, including isolated PD-L1 blockade alone.

The invention provides a method of inhibiting a malignancy associated with HPV (i.e., an HPV+ malignancy) comprising administering to a subject an agent that blocks PD-L1 and TGF-beta pathways, thereby inhibiting the HPV+ malignancy in the subject.

The HPV+ malignancy can be any cancer associated with HPV. Exemplary cancers include, but are not limited to, cervical cancer, oropharyngeal cancers (head and neck cancer, such as cancers of the back of the throat, including the base of the tongue and tonsils), rectal cancer (e.g., squamous cell rectal cancer), anal cancer, vaginal cancer, vulvar cancer, and penile cancer. In one embodiment, the HPV+ malignancy is a cancer associated with HPV16 infection. In another embodiment, the HPV+ malignancy is a cancer associated with HPV18 infection.

Any agent that blocks the PD-L1 and TGF-beta pathways can be used in the inventive method. In one embodiment, the agent blocks PD-1 and sequesters TGF-beta. For example, the agent be:

(1) a PD-L1 inhibitor: for example, a PD-L1 antibody or antibody fragment, a PD-L1 small molecule inhibitor, an antibody that targets the interaction of PD-1 with its ligands PD-L1 and PD-L2, or an antibody that inhibits PD-1 signaling. Exemplary PD-L1 inhibitors include, but are not limited to BMS-936559, MPDL3280A, MEDI4736, nivolumab (also known as BMS-936558 or MDX1106), pemborolizumab, pidilizumab, avelumab, and MK-3575 (see, e.g., Sunshine et al., Curr. Opin. Pharmacol., 23: 32-38 (2015); Weber, Semin. Oncol., 37(5): 430-4309 (2010); Tang et al., Current Oncology Reports, 15(2): 98-104 (2013); Patnaik et al., 2012 American Society of Clinical Oncology (ASCO) Annual Meeting, Abstract #2512); and ClinicalTrials.gov Identifier NCT00730639).

(2) a TGF-beta inhibitor: for example, a TGF-beta antibody or antibody fragment, a TGF-beta small molecule inhibitor, an antibody that targets the interaction of TGF-beta with its receptor, and a dominant negative form of a TGF-beta receptor. Exemplary TGF-beta inhibitors include, but are not limited to, galunisertib, SB-431542, fresolimumab, lerdelimumab, metelimumab, and the soluble extracellular domain of TGF-betaRII.

(3) combinations and fusion proteins of one or more from each of (1) and (2): for example, M7824 (MSB0011359C) (see, e.g., ClinicalTrials.gov Identifier: NCT02517398).

The agent can be a fusion protein (bifunctional fusion protein) that blocks the PD-L1 and TGF-beta pathways. The fusion protein can comprise two or more (e.g. two, three, four, five, six, or more) components, which are fused directly to each other or joined via a linker. The linker can be any suitable linker of any length, such as at least about 15 (e.g., at least about 20, at least about 25, at least about 30, at least about 35, at least about 40, at least about 45, at least about 50, or ranges thereof) amino acids in length. In one embodiment, the linker is an amino acid sequence that is naturally present in immunoglobulin molecules of the host, such that the presence of the linker would not result in an immune response against the linker sequence by the mammal. For example, the linker can comprise one or more (e.g., two or more, three or more, four or more, five or more, six or more, seven or more, eight or more, nine or more, or ten or more) $G_4S$ motifs.

In one embodiment, the fusion protein comprises (i) an antibody or antibody fragment (e.g., Fab, scFv, eAd, etc.) and (ii) a TGF-beta-neutralizing trap component. The TGF-beta-neutralizing trap component can be joined to the antibody or antibody fragment in any suitable manner, such as fused to the Fc region of the antibody or antibody fragment. The antibody or antibody fragment portion of the fusion protein can be any suitable antibody or antibody fragment, such as a human PD-L1 antibody or antibody fragment. In one embodiment, the antibody or antibody fragment is an IgG1 monoclonal antibody against human PD-L1. The TGF-beta-neutralizing trap component of the fusion protein can be any suitable TGF-beta-neutralizing trap component, such as an extracellular domain of transforming growth factor-beta (TGF-beta) receptor II (TGF-betaRII) (e.g., an extracellular domain of human TGF-betaRII that binds TGF-beta1, TGF-beta2, and/or TGF-beta3).

In a particular embodiment, the agent is M7824 (MSB0011359C), which is a bifunctional fusion protein comprised of a fully human IgG1 monoclonal antibody against PD-L1 (avelumab) fused to the soluble extracellular domain of TGF-betaRII, which acts as a TGF-beta trap. Although not wishing to be bound by any particular theory, the TGF-betaRII moiety of MSB0011359C is believed to bind to and neutralize TGF-beta while the avelumab moiety simultaneously binds to PD-L1. This prevents TGF-beta- and PD-L1-mediated signaling, and increases natural killer (NK) cell and cytotoxic T-lymphocyte (CTL) activities. This inhibits tumor cell proliferation in susceptible tumor cells.

The invention also provides a nucleic acid encoding the agent (e.g., fusion protein). The nucleic acid can comprise DNA, cDNA, and/or RNA, can be single or double stranded, and can be naturally-occurring, synthetic, and/or recombinant. Furthermore, the nucleic acid can comprise nucleotide analogues or derivatives (e.g., inosine or phophorothioate nucleotides and the like). Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (e.g., L. Stryer, 1988, Biochemistry, 3.sup.rd Edition, W. H. Freeman and Co., NY).

The nucleic acid can be provided as part of a construct comprising the nucleic acid and elements that enable delivery of the nucleic acid to a cell, and/or expression of the nucleic acid in a cell. For example, the nucleotide sequence encoding the agent (e.g., fusion protein) can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. Suitable promoters include, but are not limited to, an SV40 early promoter, RSV promoter, adenovirus major late promoter, human CMV immediate early I promoter, poxvirus promoter, 30K promoter, I3 promoter, sE/L promoter, 7.5K promoter, 40K promoter, and C1 promoter. T DNA vaccines are described in U.S. Pat. Nos. 5,589,466; 5,973,972, which are each incorporated herein by reference. In addition to the delivery protocols described in those applications, alternative methods of delivering DNA are described in U.S. Pat. Nos. 4,945,050 and 5,036,006.

A nucleic acid encoding the agent (e.g., fusion protein) can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a nucleotide sequence encoding the agent (e.g., fusion protein) can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., Cold Spring Harbor Symp. Quant. Biol. 51:263, 1987; and Erlich, ed., PCR Technology, (Stockton Press, NY, 1989). Polynucleotides also can be isolated by screening genomic or cDNA libraries with probes selected from the sequences of the desired polynucleotide under stringent hybridization conditions.

The invention further provides a vector comprising the nucleic acid. Examples of suitable vectors include plasmids (e.g., DNA plasmids), bacterial vectors, and viral vectors such as poxvirus, retrovirus, adenovirus, adeno-associated virus, herpes virus, polio virus, alphavirus, baculorvirus, and Sindbis virus. When the vector is a plasmid (e.g., DNA plasmid), the plasmid can be complexed with chitosan. When the vector is a poxviral vector, the poxvirus can be selected from the group consisting of orthopox, avipox, fowlpox, raccoon pox, rabbit pox, capripox (e.g., goat pox and sheep pox), leporipox, and suipox (e.g., swinepox). Examples of avipox viruses include fowlpox, pigeonpox, and canarypox, such as ALVAC. Examples of orthopox viruses include vaccinia, modified vaccinia Ankara (MVA), Wyeth, NYVAC, TROYVAC, Dry-Vax, PDXVAC-TC (Schering-Plough Corporation), and derivatives thereof. For example, derivatives of the Wyeth strain include, but are not limited to, derivatives which lack a functional K1L gene. When the vector is for administration to a mammalian subject (e.g., a mouse, rat, guinea pig, hamster, rabbit, cat, dog, goat, pig, cow, horse, or primate (e.g., human)), the vector (e.g., poxvirus) preferably has a low replicative efficiency in a target cell (e.g., no more than about 1 progeny per cell or, more preferably, no more than 0.1 progeny per cell are produced). Replication efficiency can readily be determined empirically by determining the virus titer after infection of the target cell.

The vector can include suitable promoters and regulatory elements, such as a transcriptional regulatory element or an enhancer. When the vector is a poxvirus vector, poxvirus promoters can be used, including but not limited to the vaccinia 7.5K promoter, vaccinia 30K promoter, vaccinia 40K promoter, vaccinia I3 promoter, synthetic early/late (sE/L) promoter, 7.5 promoter, HH promoter, 11K promoter, and Pi promoter. While the promoters typically will be constitutive promoters, inducible promoters also can be used in the inventive vectors. Such inducible systems allow regulation of gene expression.

A cell comprising the agent (e.g., fusion protein, nucleic acid, or vector) also is provided herein. Suitable cells include prokaryotic and eukaryotic cells, e.g., mammalian cells, fungi, and bacteria (such as *E. coli, Salmonella* (e.g., *S. typhimurium*), or *Listeria* (e.g., *L. monocytogenes*). Techniques for the propagation of mammalian cells in culture are well-known (see, Jakoby and Pastan (eds), 1979, Cell Culture. Methods in Enzymology, volume 58, Academic Press, Inc., Harcourt Brace Jovanovich, N.Y.). Examples of commonly used mammalian host cell lines are VERO and HeLa cells, CHO cells, and WI38, BHK, and COS cell lines, although cell lines may be used, such as cells designed to provide higher expression desirable glycosylation patterns, or other features.

Transformation of a host cell with recombinant DNA can be carried out by conventional techniques as are well known to those skilled in the art. Where the host is prokaryotic, such as, but not limited to, *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the non-yeast host cell if desired, or by electroporation.

When the cell is a eukaryote, such methods of transfection of DNA as calcium phosphate coprecipitates, conventional mechanical procedures such as microinjection, electroporation, insertion of a plasmid encased in liposomes, or infection with virus vectors can be used. Eukaryotic cells can also be co-transformed with polynucleotide sequences encoding the agent, and a second foreign DNA molecule encoding a selectable phenotype, such as the herpes simplex thymidine kinase gene. Methods for using viral vectors to transform eukaryotic cells are known, (see for example, Eukaryotic Viral Vectors, Cold Spring Harbor Laboratory, Gluzman ed., 1982).

The agent (e.g., fusion protein, nucleic acid, or vector) can be administered alone or in a composition (e.g., pharmaceutical composition) that can comprise at least one carrier (e.g., a pharmaceutically acceptable carrier). Alternatively, or in addition, the composition can comprise one or more other active (e.g., therapeutic or prophylactic) agents or drugs. Examples of such other active agents or drugs that may be suitable for use in the pharmaceutical composition include anticancer agents (e.g., chemotherapeutic drugs), antibiotics, antiviral drugs, antifungal drugs, cyclophosphamide, anti-inflammatory agents, immunotherapy, and combinations thereof. Suitable anticancer agents include, without limitation, alkylating agents, nitrogen mustards, folate antagonists, purine antagonists, pyrimidine antagonists, spindle poisons, topoisomerase inhibitors, apoptosis inducing agents, angiogenesis inhibitors, podophyllotoxins, nitrosoureas, cisplatin, carboplatin, interferon, asparginase, tamoxifen, leuprolide, flutamide, megestrol, mitomycin, bleomycin, doxorubicin, irinotecan, taxol, geldanamycin (e.g., 17-AAG), and various anti-cancer polypeptides and antibodies known in the art.

The pharmaceutically acceptable carrier (or excipient) is preferably one that is chemically inert to the agent and one that has no detrimental side effects or toxicity under the conditions of use. Such pharmaceutically acceptable carriers include, but are not limited to, water, saline, Cremophor EL (Sigma Chemical Co., St. Louis, Mo.), propylene glycol, polyethylene glycol, alcohol, and combinations thereof. The choice of carrier will be determined in part by the particular agent, as well as by the particular method used to administer the composition. Accordingly, there is a wide variety of suitable formulations of the composition.

The term "immunotherapy," as used herein refers to the treatment of a disease by inducing, enhancing, or suppressing an immune response. Immunotherapies designed to elicit or enhance an immune response are referred to as activation immunotherapies, while immunotherapies designed to suppress an immune response are referred to suppression immunotherapies. Types of immunotherapies include, but are not limited to, immunomodulators, cell-based immunotherapies, monoclonal antibodies, radiopharmaceuticals, and vaccines. Immunotherapy strategies for cancer are described in, for example, Waldmann, T. A., *Nature Medicine,* 9: 269-277 (2003).

Immunomodulators can be recombinant, synthetic, or natural substances that include, but are not limited to, cytokines (e.g., TNF-α, IL-6, GM-CSF, IL-2, and interferons), co-stimulatory molecules (e.g., B7-1 and B7-2), chemokines (e.g., CCL3, CCL26, CXCL7), glucans, and oligodeoxynucleotides.

Cell-based immunotherapies typically involve removal of immune cells (e.g., cytotoxic T-cells, natural killer cells, or antigen presenting cells (APCs)) from a subject, modification (e.g., activation) of immune cells, and return of the modified immune cells to the patient. The cell-based immunotherapy can be Sipuleucel-T (PROVENGE™), which is an autologous active cellular immunotherapy used in the treatment of asymptomatic or minimally symptomatic CRPC (Plosker, G. L., *Drugs,* 71(1): 101-108 (2011); and Kantoff et al., *New Engl. J. Med.,* 363: 411-422 (2010)).

Several monoclonal antibodies have been approved for the treatment of cancer, including naked antibodies and antibody-drug conjugates based on human, humanized, or chimeric antibodies (Scott et al., *Nat Rev Cancer,* 12(4): 278-87 (2012); Harding et al., *MAbs,* 2(3): 256-65 (2010); and Weiner et al., *Nature Rev. Immunol.,* 10(5): 317-327 (2010)).

Radiopharmaceuticals are radioactive drugs which are currently used to treat and diagnose a variety of diseases, including cancer. For example, radionuclides can be targeted to antibodies (i.e., radioimmunotherapy) to treat blood-derived cancers (Sharkey, R. M. and Goldenberg, D. M., *Immunotherapy,* 3(3): 349-70 (2011)). Several radioisotopes have been approved to treat cancer, including iodine-125, iodine-131, and radium-223 (marketed as XOFIGO™). Radium-223 has been approved as a radiopharmaceutical to treat metastatic bone cancer and CRPC. In CRPC, radium-223 also has been shown to enhance the anti-tumor immune response.

Vaccines represent another strategy to prevent and treat cancer. Many different cancer vaccine platforms are currently being evaluated in phase II and/or phase III clinical trials, including, for example, peptide-based vaccines, recombinant viral vectors, killed tumor cells, or protein-activated dendritic cells (see, e.g., Schlom, J., *J. Natl. Cancer. Inst.,* 104: 599-613 (2012)). In one embodiment, the vaccine can be a Brachyury vaccine, which comprises recombinant yeast or poxvirus that has been genetically modified to express the Brachyury transcription factor (see, e.g., International Patent Application Publications WO 2014/043518 and WO 2014/043535; and U.S. Pat. Nos. 8,188,214 and 8,613,933).

The agent (e.g., fusion protein, nucleic acid, or vector) or composition thereof is useful for preventing emergence of cancers, arresting progression of cancers, or eliminating cancers. More particularly, the agent can be used to prevent, inhibit or delay the development of tumors, and/or to prevent, inhibit or delay tumor migration and/or tumor invasion of other tissues (metastases) and/or to generally prevent or inhibit progression of cancer in an individual. The agent or composition thereof can also be used to ameliorate at least one symptom of the cancer, such as by reducing tumor burden in the individual; inhibiting tumor growth in the individual; increasing survival of the individual; and/or preventing, inhibiting, reversing or delaying progression of the cancer in the individual.

The tumor can be at any stage, and can be subject to other therapies. The inventive method is useful in treating tumors (i.e., destruction of tumor cells or reduction in tumor size), such as tumors that have been proven to be resistant to other forms of cancer therapy, such as radiation-resistant tumors. The tumor also can be of any size. Ideally, the inventive method results in cancerous (tumor) cell death and/or reduction in tumor size. It will be appreciated that tumor cell death can occur without a substantial decrease in tumor size due to, for instance, the presence of supporting cells, vascularization, fibrous matrices, etc. Accordingly, while reduction in tumor size is preferred, it is not required in the treatment of cancer.

When the agent is administered with one or more additional active agents (e.g., anti-inflammatory agents and/or chemotherapeutic agents), the agent and one or more additional active agents can be coadministered to the mammal. By "coadministering" is meant administering one or more additional active agents and the agent sufficiently close in time such that the agent can enhance the effect of one or more additional active agents. In this regard, the agent can be administered first and the one or more additional active agents can be administered second, or vice versa. Alternatively, the agent and the one or more additional active agents can be administered simultaneously.

The agent or composition can be administered by any suitable route, including parenteral, topical, oral, or local administration. The following formulations for oral, aerosol, parenteral (e.g., subcutaneous, intravenous, intraarterial, intramuscular, intradermal, interperitoneal, and intrathecal), rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The agent alone or in combination with other suitable components, can be made into aerosol formulations to be administered via inhalation. These aerosol fonnulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The agent can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets.

The agent can be administered as an injectable formulation. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Topical formulations, including those that are useful for transdermal drug release, are well known to those of skill in the art and are suitable in the context of the invention for application to skin.

The agent can be administered as a suppository by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

The concentration of a compound of the present invention in the pharmaceutical formulations can vary, e.g., from less than about 1%, usually at or at least about 10%, to as much as 20% to 50% or more by weight, and can be selected primarily by fluid volumes, and viscosities, in accordance with the particular mode of administration selected.

Methods for preparing administrable (e.g., parenterally administrable) agents are known or apparent to those skilled in the art and are described in more detail in, for example, *Remington's Pharmaceutical Science* (17th ed., Mack Publishing Company, Easton, Pa., 1985).

In addition to the described pharmaceutical compositions, the agent can be formulated as inclusion complexes, such as cyclodextrin inclusion complexes, or liposomes. Liposomes can serve to target the agent to a particular tissue. Liposomes also can be used to increase the half-life of the agent. Many methods are available for preparing liposomes, as described in, for example, Szoka et al., *Ann. Rev. Biophys. Bioeng.*, 9, 467 (1980) and U.S. Pat. Nos. 4,235,871, 4,501,728, 4,837, 028, and 5,019,369.

The following examples further illustrate the invention but, of course, should not be construed as in any way limiting its scope.

EXAMPLE 1

This example demonstrates that blockade of the PD-L1 and TGF-beta pathways results in an inhibition of malignancies associated with HPV.

M7824 (MSB0011359C) is a bifunctional fusion protein comprised of a fully human IgG1 monoclonal antibody against programmed death ligand 1 (PD-L1) fused to the soluble extracellular domain of transforming growth factor-beta (TGF-beta) receptor II, which acts as a TGF-beta trap.

A phase 1 trial of M7824 (MSB0011359C) in advanced solid tumors was undertaken. NCT02517398 is a phase 1, open-label, 3+3 dose-escalation study. Eligible patients received M7824 at 1, 3, 10, 20, or 30 mg/kg Q2W until confirmed progressive disease or unacceptable toxicity. The primary objective was to determine the safety and maximum tolerated dose of M7824, and secondary objectives include phamacokinetics (PK), immunogenicity, and best overall response per RECIST v1.1.

Patients with advanced cancer were treated, including 16 patients with HPV-associated malignancies (9 cervical, 4 anal, and 3 P16+ head & neck squamous cell carcinoma (HNSCC)). HPV status was positive in 11 of the patients and unknown in the other 5 patients. Grade 3 drug-related treatment-emergent adverse events (TEAEs) occurred in 3 of these 16 patients (colitis, cystitis, and gastroparesis; all in cervical patients). Notably all three of these patients also had evidence of clinical benefit with disease reduction. There was one grade 4 TEAE of hypokalemia associated with the grade 3 gastroparesis. Otherwise no other grade 4-5 TEAEs were noted. The only dose-limiting toxicity (DLT) observed was colitis at a dose of 20 mg/kg and no maximum-tolerated dose (MTD) was reached at the doses studied.

Of the 16 patients, 9 (56%) have had disease reduction on treatment including 1 patient (cervical; HPV+) with a durable complete response (CR); 4 patients (2 HNSCC, 2 anal; all HPV+) with durable partial responses (PRs), 1 patient (cervical; HPV unknown) with an unconfirmed PR, 2 patients (2 cervical; both HPV unknown) with near PRs (−25%, −27%) and 1 patient (anal; HPV unknown) with more modest disease reduction (−9%).

Overall for patients with HPV+ or unknown status, $6/16$ (37.5%) have ongoing responses, with $5/6$ of these responses being confirmed to date, and for patients with known HPV+ disease, $5/11$ (45.5%) have ongoing confirmed responses. Preliminary data from a subset of patients with HPV-associated malignancies enrolled in the phase 1 trial suggest a manageable safety profile with an overall response rate (ORR) of 37.5% among patients with HPV+ or unknown status and a confirmed ORR of 45.5% among patients with known HPV+ disease.

Based on the results of the ongoing phase I clinical trial, it is apparent that dual blockade of PD-L1 and TGF-beta pathways (e.g., by M7824 that blocks PD-L1 and sequesters TGF-beta) has the potential to produce significantly high response rates in patients who have HPV+ malignancies. Early evidence from this trial suggests that blockade of these two pathways produces response rates much higher than any current treatment, including isolated PD-L1 blockade alone, for patients with advanced HPV+ cancers who have progressed or are intolerant to standard first line therapies.

Therefore, evidence suggests that blockade of these two pathways in unison produces response rates much higher than any current treatment, including isolated PD-L1 blockade alone, for patients with advanced HPV+ cancers who have progressed or are intolerant to standard first line therapies. Simultaneous blockade of these two pathways has a substantial clinical benefit for these patients and will have a substantial clinical impact in the near future.

EXAMPLE 2

This example provides a design for a phase II trial of M7824 in subjects with HPV+ malignancies.

The PD-L1 and TGF-beta pathways are two key immune evasion pathways that have independent and complementary immunosuppressive functions. Dual targeting of the PD-L1 and TGF-beta pathways results in synergistic antitumor activity.

Rationale. Metastatic or refractory/recurrent HPV associated malignancies (cervical, anal, oropharyngeal cancers etc.) are incurable and poorly palliated by standard therapies. Single agent PD-1 inhibitors have produced a response rate in the range of 12-20% for these diseases. Pembrolizumab, a monoclonal antibody that blocks PD-1, was recently FDA approved for recurrent or metastatic head and neck squamous cell carcinoma (HNSCC) based upon a 16% response rate (28/174 patients) in the phase 1b KEYSTONE 012 trial. Response rates were similar between HPV positive and HPV negative HNSCC. A phase 1b trial (KEYSTONE 028) showed a 12.5% response rate (3/24 patients) to pembrolizumab in patients with recurrent or metastatic cervical cancer and a 20% response rate (5/25) in patients with recurrent or metastatic squamous cell cancer of the anal canal. Early data from a small cohort of patients with HPV associated malignancies in a phase 1 trial of M7824 (MSB0011359C) suggests that this agent, which targets both PD-L1 and TGF-beta pathways, produces responses at a higher rate as compared with other single agent PD-1/PD-L1 inhibitors in this patient population.

Objectives. The primary objective is to determine the objective response rate of M7824 in patients with recurrent or metastatic HPV positive malignancies in five subpopulations: patients with anal cancer naïve to checkpoint inhibition, patients with anal cancer refractory to checkpoint inhibition, patients with cervical cancer refractory to checkpoint inhibition, patients with P16+ head and neck cancer refractory to checkpoint inhibition, and patients with rare HPV associated tumors (squamous cell rectal, vulvar, vaginal, penile cancer) naïve to checkpoint inhibition The secondary objective is to conduct exploratory immunologic studies to understand and improve the administered treatment including but not limited to: assessment of circulating tumor cells, assessment of circulating tumor DNA, assessment of antigen specific T cell responses to E6/E7 oncoproteins, peripheral immune subset analysis, T cell receptor analysis, and HPV typing.

Eligibility. Eligibility for the phase II trial includes patients greater than or equal to 18 years old with metastatic or refractory/recurrent HPV associated malignancies, cervical cancers (99% are HPV+), P16+ oropharyngeal cancers, anal cancers (90% are HPV+), squamous cell rectal cancer (90% are HPV+), or vulvar, vaginal, and penile cancers with positive HPV testing (60-70% are HPV+). Although positive HPV testing will be required only for patients with vulvar, vaginal and penile cancers prior to enrolling, HPV testing will be done as an exploratory endpoint on all other tumor types and patients testing negative for HPV will be replaced. Prior first line systemic therapy is required unless the patient declines standard treatment.

Design. All patients will receive 1200 mg of M7824 IV over 60 min every 2 weeks until PD or toxicity. There will be five cohorts: (1) patients with anal cancer naïve to checkpoint inhibition, (2) patients with anal cancer refractory to checkpoint inhibition, (3) patients with cervical cancer refractory to checkpoint inhibition, (4) patients with P16+ head and neck cancer refractory to checkpoint inhibition, (5) patients with rare HPV associated tumors (squamous cell rectal, vulvar, vaginal, penile cancer) naïve to checkpoint inhibition. All 5 cohorts of the trial will be conducted using a Simon two-stage phase II trial design.

For both of the immune checkpoint naïve cohorts (anal and rare tumor type), the first stage will enroll 8 evaluable patients, and if 2 or more of the 8 have an objective response, then accrual would continue until a total of 13 evaluable patients have been treated. If there are 4 or more of 13 (30.8%) who experience a response, this would be sufficiently interesting to warrant further study in later trials.

For all three of the immune checkpoint refractory cohorts (anal, cervical, head & neck), the first stage will enroll 8 evaluable patients, and if 1 or more of the 8 have an objective response, then accrual would continue until a total of 12 evaluable patients have been treated. If there are 2 or more of 12 (16.7%) who experience a response, this would be sufficiently interesting to warrant further study in later trials.

Statistical considerations. The primary objective of this trial is to determine the objective response rate to a combined anti PD-L1/TGF beta inhibitor in patients with HPV positive cancers. Patients will be enrolled into five cohorts: (1) patients with anal cancer naïve to checkpoint inhibition, (2) patients with anal cancer refractory to checkpoint inhibition, (3) patients with cervical cancer refractory to checkpoint inhibition, (4) patients with P16+ head and neck cancer refractory to checkpoint inhibition, (5) patients with rare HPV associated tumors (squamous cell rectal, vulvar, vaginal, penile cancer) naïve to checkpoint inhibition.

For the two cohorts naïve to anti PD-1/PD-L1 therapy (anal and rare tumor type), data from the literature (at least with anal cancer) suggest that a response rate for a single agent PD-1/PD-L1 treatment may be approximately 15-20%. This trial will try to demonstrate if the proposed therapy may be associated with an improved response rate.

In order to establish the efficacy of this treatment in patients naïve to therapy, the primary objective in these two cohorts would be to determine if using the proposed agent would rule out a 15% response rate and result in a response rate consistent with 40%. As such, each of the three disease-specific cohorts in naïve patients will be conducted using a Simon minimax two-stage phase II trial design (Simon R, Controlled Clinical Trials 10:1-10, 1989) in order to rule out an unacceptably low PR+CR rate of 15% (p0=0.15) in favor of an improved response rate of 40% (p1=0.40). Aiming to keep the cohorts deliberately small, with alpha=0.15 (probability of accepting a poor treatment=0.15) and beta =0.20 (probability of rejecting a good treatment=0.20), the first stage in each disease-based naïve cohort will enroll 8 evaluable patients, and if 0 to 1 of the 8 have a clinical response, then no further patients will be accrued in that cohort. If 2 or more of the first 8 patients have a response, then accrual would continue until a total of 13 evaluable patients naïve to therapy have been treated in each cohort. As it may take up to several months to determine if a patient has experienced a response, a temporary pause in the accrual may be necessary to ensure that enrollment to the second stage is warranted. If there are 2 to 3 patients with a response out of 13 patients, this would be an uninterestingly low response rate for that cohort. If there were 4 or more of 13 (30.8%) who experienced a response, this would be sufficiently interesting to warrant further study in later trials in that disease type. Under the null hypothesis (15% response rate), the probability of early termination is 65.7%.

For the three cohorts refractory to anti PD-1/PD-L1 therapy (anal, cervical, head & neck), there is limited information in the published literature regarding potential response rates in this population, but it is expected to be low. A response rate clearly exceeding 5% would be of interest to obtain.

In order to establish the efficacy of this treatment in patients who are refractory to therapy, the primary objective in these three cohorts would be to determine if using the proposed agent would rule out a 5% response rate and result in a response rate consistent with 25%. As such, each of the three disease specific cohorts in refractory patients will be conducted using a Simon minimax two-stage phase II trial design (Simon R, Controlled Clinical Trials 10:1-10, 1989) in order to rule out an unacceptably low PR+CR rate of 5% (p0=0.05) in favor of an improved response rate of 25% (p1=0.25). With alpha=0.15 (probability of accepting a poor treatment=0.10) and beta =0.20 (probability of rejecting a good treatment=0.20), the first stage in each disease-based cohort will enroll 8 evaluable patients, and if 0 of the 8 have a clinical response, then no further patients will be accrued in that cohort. If 1 or more of the first 8 patients have a response, then accrual would continue until a total of 12 evaluable patients who are refractory to therapy have been treated in each cohort. As it may take up to several months to determine if a patient has experienced a response, a temporary pause in the accrual may be necessary to ensure that enrollment to the second stage is warranted. If there is one patient with a response out of 12 patients, this would be an uninterestingly low response rate in that cohort. If there were 2 or more of 12 (16.7%) who experienced a response, this would be sufficiently interesting to warrant further study in later trials in that disease type. Under the null hypothesis (5% response rate), the probability of early termination is 66.3%.

It should be noted that in all of these cases, patients will undergo definitive HPV testing after they have undergone treatment; it is anticipated that perhaps 5-10% of all patients enrolled onto the trial will be HPV negative despite their clinical diagnosis. These patients will be replaced with other presumably HPV positive patients, and the replacement patients will be the ones which will be included in the final analyses. This may mean, in an unusual but plausible situation, that accrual to a second stage may take place on the basis of a response in an HPV negative patient, but for which the replacement was not a responder. This has the unintended consequence of continuing to the second stage when in fact there were inadequate responses in eligible patients in the first stage. As a remedy, the trial will end accrual to the second stage on the basis of the new information learned as soon as the determination is made, even if it means that accrual of one or more patients took place to the second stage on the basis of an overstatement of the responses in the first stage. In order to allow for the possibility of inevaluable patients on the basis of being HPV negative or for other reasons, the trial will allow for up to 8 inevaluable patients.

It is expected that approximately 3 patients per month may enroll onto this trial. Thus, it is expected that 2 years may be required in order to enroll up to 26 evaluable naïve plus 36 evaluable refractory patients (62 total evaluable patients). In order to allow for a small number of inevaluable patients, including those who are retrospectively determined to be HPV negative, the accrual ceiling will be set at 70 patients.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of inhibiting a malignancy associated with human papilloma virus (HPV) comprising administering to a subject an agent or combination of agents that blocks PD-L1 and TGF-beta pathways, thereby inhibiting a malignancy associated with HPV in the subject.

2. The method of claim 1, wherein the agent blocks PD-1 and sequesters TGF-beta.

3. The method of claim 1, wherein the agent is a fusion protein.

4. The method of claim 3, wherein the fusion protein comprises (i) a PD1 inhibitor and (ii) a TGF-beta inhibitor.

5. The method of claim 4, wherein the PD1 inhibitor is an antibody or antibody fragment.

6. The method of claim 5, wherein the antibody or antibody fragment is a human PD-L1 antibody.

7. The method of claim 5, wherein the antibody or antibody fragment is an IgG1 monoclonal antibody against human PD-L1.

8. The method of claim 7, wherein the antibody or antibody fragment is avelumab.

9. The method of claim 5, wherein the TGF-beta inhibitor is fused to the Fc region of the antibody or antibody fragment.

10. The method of claim 4, wherein TGF-beta inhibitor is an extracellular domain of human TGF-betaRII.

11. The method of claim 10, wherein the extracellular domain of human TGF-betaRII is a soluble extracellular domain of TGF-betaRII.

12. The method of claim 3, wherein the fusion protein is administered as a nucleic acid encoding the fusion protein.

13. The method of claim 12, wherein the nucleic acid encoding the fusion protein is in a vector.

14. The method claim 13, wherein the vector is a plasmid or viral vector.

15. The method of claim 14, wherein the vector is a viral vector selected from the group consisting of poxvirus, retrovirus, adenovirus, adeno-associated virus, herpes virus, polio virus, alphavirus, baculorvirus, and Sindbis virus.

16. The method of claim 15, wherein the viral vector is a poxvirus selected from the group consisting of orthopox, avipox, fowlpox, raccoon pox, rabbit pox, capripox, leporipox, and suipox.

17. The method of claim 1, wherein the agent is M7824 (MSB0011359C).

18. The method of claim 1, wherein the agent is administered in a composition comprising the agent and a pharmaceutically acceptable carrier.

19. The method of claim 18, wherein the composition further comprises one or more additional active agents.

20. The method of claim 19, wherein the one or more additional active agents are selected from the group consisting of anticancer agents, antibiotics, antiviral drugs, antifungal drugs, cyclophosphamide, anti-inflammatory agents, immunotherapy, and combinations thereof.

21. The method of claim 1, wherein the subject is a human subject.

22. The method of claim 1, wherein the malignancy associated with HPV is selected from the group consisting of cervical cancer, oropharyngeal cancers, rectal cancer, anal cancer, vaginal cancer, vulvar cancer, penile cancer, and HPV-positive cancer.

* * * * *